United States Patent [19]

Nedelec et al.

[11] 4,154,852
[45] May 15, 1979

[54] NOVEL AMINOBENZOCYCLOHEPTENES

[75] Inventors: Lucien Nedelec, Le Raincy; Daniel Frechet, Paris; Claude Dumont, Nogen-sur-Marne, all of France

[73] Assignee: Roussel Uclaf, Paris, France

[21] Appl. No.: 835,171

[22] Filed: Sep. 20, 1977

[30] Foreign Application Priority Data

Sep. 23, 1976 [FR] France .............................. 76 28614

[51] Int. Cl.$^2$ ..................... A01N 9/20; C07C 87/64; C07C 91/28; C07C 93/14
[52] U.S. Cl. .............................. 424/330; 260/326.81; 260/574; 260/577; 260/590 FA; 424/248.4; 424/248.58; 424/250; 424/267; 424/274; 424/316; 544/174; 544/178; 544/398; 544/401; 544/403; 546/205; 546/206
[58] Field of Search ..................... 260/574, 577, 570.9, 260/585 D, 571; 424/316, 330

[56] References Cited

U.S. PATENT DOCUMENTS

| | | | |
|---|---|---|---|
| 2,794,048 | 5/1957 | Richter | 260/570.9 |
| 2,984,687 | 5/1961 | Esmay et al. | 260/577 |
| 3,201,470 | 8/1965 | Huebner | 260/577 |
| 3,513,200 | 5/1970 | Biale | 260/585 D X |
| 3,751,420 | 8/1973 | Hauck et al. | 260/571 X |
| 4,091,115 | 5/1978 | Nedelec et al. | 424/330 |

OTHER PUBLICATIONS

Carlsson et al., "Chem. Ab.", vol. 63, Ab. No. 2276$^a$, (1965).

*Primary Examiner*—Patrick Garvin
*Assistant Examiner*—John Doll
*Attorney, Agent, or Firm*—Hammond & Littell

[57] ABSTRACT

Novel 7-aminobenzocycloheptenes of the formula

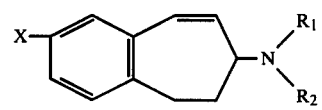

wherein X is selected from the group consisting of —NO$_2$, —NH$_2$, CH$_3$O— and —OH, R$_1$ is selected from the group consisting of hydrogen and alkyl of 1 to 5 carbon atoms, R$_2$ is alkyl of 1 to 5 carbon atoms and R$_1$ and R$_2$ together with the nitrogen atom to which they are attached form a saturated heterocycle of 4 to 6 ring carbon atoms optionally containing a second heteroatom in the ring and optionally substituted with an alkyl of 1 to 5 carbon atoms and their non-toxic, pharmaceutically acceptable acid addition salts in optically active or racemic mixture form having antidepressant activity and a process for their preparation.

15 Claims, No Drawings

NOVEL AMINOBENZOCYCLOHEPTENES

STATE OF THE ART

U.S. Pat. No. 3,751,420 and copending, commonly assigned U.S. patent applications Ser. Nos. 708,749 and 708,750, both filed on July 26, 1976 describe 7-aminobenzocycloheptanes but they have a different structure.

OBJECTS OF THE INVENTION

It is an object of the invention to provide the novel 7-aminobenzocycloheptenes of formula I and their non-toxic, pharmaceutically acceptable acid addition salts and a novel process for their preparations.

It is a further object of the invention to provide novel antidepressant compositions and a novel method of alleviating depression in warm-blooded animals.

These and other objects and advantages of the invention will become obvious from the following detailed description.

THE INVENTION

The novel compounds of the invention are selected from the group consisting of 7-aminobenzocycloheptenes of the formula

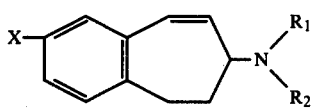

wherein X is selected from the group consisting of —$NO_2$, —$NH_2$, $CH_3O$— and —OH, $R_1$ is selected from the group consisting of hydrogen and alkyl of 1 to 5 carbon atoms, $R_2$ is alkyl of 1 to 5 carbon atoms and $R_1$ and $R_2$ together with the nitrogen atom to which they are attached form a saturated heterocycle of 4 to 6 carbon atoms optionally containing a second heteroatom in the ring and optionally substituted with an alkyl of 1 to 5 carbon atoms and their non-toxic, pharmaceutically acceptable acid addition salts in optically active or racemic mixture form.

Examples of alkyl groups of the compounds of formula I are methyl, ethyl, propyl, isopropyl, butyl, isobutyl and pentyl and examples of heterocycle groups of the compounds are pyrrolidino, piperidino, morpholino, piperazinyl, N-methyl-piperazinyl, N-ethyl-piperazinyl, N-propyl-piperazinyl and N-butyl-piperazinyl.

Examples of suitable acids to form the non-toxic, pharmaceutically acceptable acid addition salts are inorganic acids such as hydrochloric acid, hydrobromic acid, hydroiodic acid, nitric acid, sulfuric acid or phosphoric acid and organic acids such as acetic acid, formic acid, benzoic acid, maleic acid, fumaric acid, succinic acid, tartaric acid, citric acid, oxalic acid, glyoxylic acid, aspartic acid, alkanesulfonic acids such as methane sulfonic acid and ethane sulfonic acid as well as arylsulfonic acids such as benzenesulfonic acid or p-toluene sulfonic acid and arylcarboxylic acids.

Among the preferred compounds of formula I are those wherein $R_1$ is hydrogen or methyl and $R_2$ is methyl and especially those wherein $R_1$ is hydrogen and $R_2$ is methyl and their non-toxic, pharmaceutically acceptable acid addition salts.

The compounds of formula I contain an asymetrical carbon atom and therefore have 2 enantiomeric forms.

The compounds may be in the form of a racemic mixture or as optically active isomers by the usual resolution methods.

The novel process of the invention for the preparation of the compounds of formula I comprises reacting a compound of the formula

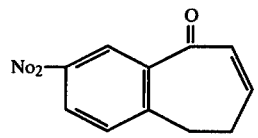

with an amine of the formula

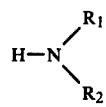

wherein $R_1$ and $R_2$ have the above definition to form a compound of the formula

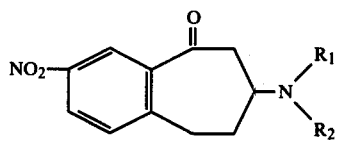

reducing the latter to obtain a compound of the formula

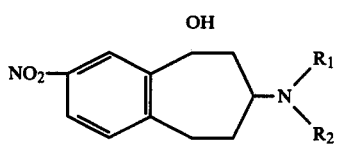

deshydrating the latter to obtain a compound of the formula

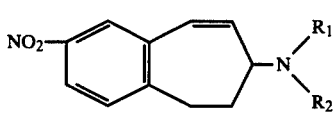

and recovering the said product or reducing the latter with a selective reducing agent to obtain a compound of the formula

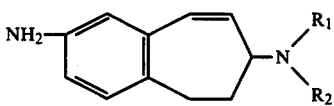

which can be recovered per se or reacted further with nitrosyl sulfuric acid to obtain the corresponding diazonium salt which is reacted with methanol to obtain a compound of the formula

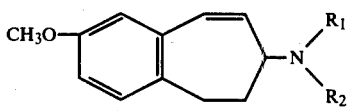

which can be recovered or the compound of formula Ib may be reacted with sodium nitrite in a sulfuric acid media to obtain the salt of the corresponding diazonium compound which is decomposed to obtain a compound of the formula

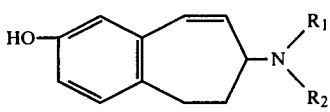

The compounds of formula Ia, Ib, Ic and Id may be salified, if desired, with substantially stoichiometric amounta of an acid with or without isolation of the base.

In a preferred mode of the process, the reaction of compounds II and III is effected at room temperature in a low molecular weight alkanol such as methanol or ethanol and the reduction of the compound of formula IV is preferably effected with sodium borohydride in the presence of a low molecular weight alkanol such as methanol or ethanol or with diborane in an organic solvent such as tetrahydrofuran. The deshydration of the compound of formula V is preferably effected with polyphosphoric acid, potassium bisulfate or a strong acid such as hydrochloric acid or sulfuric acid in an organic solvent such as dioxane. The selective reduction of a compound of formula Ia is effected with a mixture of reducing agents such as a mixture of stannous chloride and hydrochloric acid. The reaction of a compound of formula Ib with nitrosyl sulfuric acid is effected in an acetic acid medium and the decomposition of the diazonium salt is effected with sulfuric acid.

The starting compounds of formula II may be prepared by reacting a compound of the formula

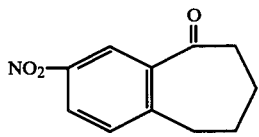

with cuprous bromide or bromine or a complex of bromine in an organic solvent to obtain a compound of the formula

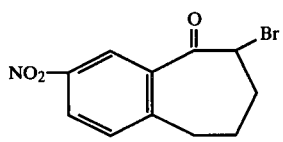

and dehydrobrominating the latter in the presence of a mixture of lithium bromide and lithium carbonate to form the compound of formula II. The brominating agent is preferably a complex of bromine such as pyridinium perbromide.

The novel antidepressant compositions of the invention are comprised of an antidepressantly effective amount of at least one compound selected from a compound of formula I and its non-toxic, pharmaceutically acceptable acid addition salts and an inert pharmaceutical carrier. The compositions may be in the form of tablets, dragees, gelules, granules, suppositories or injectable solutions or suspensions prepared in the usual manner.

Examples of suitable excipients or pharmaceutical carriers are talc, arabic gum, lactose, starch, magnesium stearate, cacao butter, aqueous or non-aqueous vehicles, fatty bodies of animal or vegetable origin, paraffinic derivatives, glycols, diverse wetting agents, dispersants or emulsifiers and preservatives.

The compositions are useful for the treatment of depression, melancholy, manic-depressive psychosis, reaction and exhaustive depressions, neurotic depression and for the treatment of Parkinson disease.

Among the preferred compositions of the invention are those wherein $R_1$ is hydrogen or methyl and $R_2$ is methyl and especially those wherein $R_1$ is hydrogen and $R_2$ is methyl and their non-toxic, pharmaceutically acceptable acid addition salts. Particularly preferred are 2-nitro-6,7-dihydro-7-methylamino [5H] benzocycloheptene, 2-amino-6,7-dihydro-7-methylamino [5H] benzocycloheptene, 2-methoxy-6,7-dihydro-7-methylamino [5H] benzocycloheptene and 6,7-dihydro-7-methyl-amino [5H] benzocycloheptene-2-ol and their non-toxic, pharmaceutically acceptable acid addition salts.

The novel method of the invention for combatting depression in warm-blooded animals, including humans, comprises administering to warm-blooded animals an antidepressantly effective amount of at least one compound of formula I and their non-toxic, pharmaceutically acceptable acid addition salts. The compounds may be administered orally, rectally, or parenterally and the usual effective daily dose is 0.2 to 6 mg/kg depending upon the specific compound and the method of administration.

Among the novel intermediates of the invention are the compounds of formulae II, IV and V and especially 3-nitro-7-methylamino-6,7,8,9-tetrahydro[5H] benzocycloheptene-5-one and 3-nitro-7-methylamino-6,7,8,9-tetrahydro [5H] benzocycloheptene-5-ol. The compounds of formula VI may be prepared as described in J. Org. Chem., Vol. 26 (1961), p. 27.

In the following examples there are described several preferred examples to illustrate the invention. However, it should be understood that the invention is not intended to be limited to the specific embodiments.

EXAMPLE 1

2-nitro-6,7-dihydro-7-methylamino [5H] benzocycloheptenehydrochloride

STEP A:

6-bromo-3-nitro-6,7,8.9-tetrahydro [5H] benzocycloheptene-5-one

A solution of 430 g of 3-nitro-6,7,8,9-tetrahydro [5H] benzocycloheptene-5-one in 2.150 liters of chloroform was added to a refluxing mixture of 935 g of cuprous bromide in 2.150 liters of ethyl acetate and after 5 minutes, the reaction began and the reflux became very strong. After one hour, the mixture was cooled to 20° C. and was vacuum filtered. The filter was washed with chloroform and the filtrate was added to 3 liters of aqueous saturated sodium bicarbonate solution. The mixture was stirred and decanted and the organic phase was dried over sodium sulfate and evaporated to dryness under reduced pressure. The residue was empasted 3 times with 450 ml of isopropyl ether and was dried at 35° C. to obtain 548 g of 6-bromo-3-nitro-6,7,8,9-tetrahydro [5H] benzocycloheptene-5-one in the form of cream crystals melting at 105° C.

STEP B:

3-nitro-8,9-dihydro [5H] benzocycloheptene-5-one

A mixture of 548 g of lithium carbonate, 548 g of lithium bromide and 5.480 liters of dimethylformamide was heated to 100° C. and 548 g of the product of Step A was added thereto over 5 minutes. The mixture was held at 100° C. for 45 minutes and was then poured into 25 liters of a water-ice-mixture. The mixture was vacuum filtered and the insolubles were extracted 8 times with one liter of methylene chloride. The organic phase was washed with water, dried over sodium sulfate and evaporated to dryness under reduced pressure. The red crystalline mass was empasted successively 3 times with 400 ml of ether, once with 400 ml of ethanol and once with 400 ml of ether and was dried at 40° C. to obtain 286.7 g of 3-nitro-8,9-dihydro [5H] benzocycloheptene-5-one in the form of red-orange crystals melting at 128° C.

STEP C:

3-nitro-7-methylamino-6,7,8,9-tetrahydro [5H] benzo cycloheptene-5-one

A solution of 101.5 g of extemporaneously prepared monomethylamine in 700 ml of benzene was added at 20° C. with stirring to a mixture of 101.6 g of the product of Step B in 1 liter of ethanol and the mixture was stirred for 2 ½ hours at room temperature and was allowed to stand for 12 hours. The mixture was evaporated to dryness under reduced pressure to obtain 125 g of 3-nitro-7-methylamino-6,7,8,9-tetrahydro [5H] benzocycloheptene-5-one in the form of a brown oil.

STEP D:

3-nitro-7-methylamino-6,7,8,9-tetrahydro [5H] benzocycloheptene-5-ol

A solution of 125 g of sodium borohydride in 625 ml of water at 10° C. was added to a solution of 125 g of the product of Step C in 2 liters of ethanol kept at 25°–30° C. and the mixture was stirred for one hour and let stand for 12 hours. The mixture was concentrated to 0.5 liters and 0.5 liters of water was added thereto. The mixture was extracted 4 times with 250 ml of methylene chloride and the combined organic extracts were extracted 3 times with 200 ml of 2 N hydrochloric acid. The aqueous acid phase was washed with 200 ml of methylene chloride and made alkaline with excess ammonium hydroxide at 10° C. The mixture was extracted 5 times with 200 ml of methylene chloride and the combined organic phases was dried over sodium sulfate and evaporated to dryness to obtain 103 g of raw product. The latter was added to 1.5 liters of a 2-1 ether-ethyl acetate mixture and 10 g of activated carbon was added thereto. The mixture was filtered and the filtrate was evaporated to dryness under reduced pressure to obtain 95 g of 3-nitro-7-methylamino-6,7,8,9-tetrahydro [5H] benzocycloheptene-5-ol in the form of a brown resin.

STEP E:

2-nitro-7-methylamino-6,7-dihydro [5H] benzocycloheptene hydrochloride

A mixture of 36 g of the product of Step D and 72 g of monopotassium sulfate was heated at 210° C. in a metallic bath with stirring for 20 minutes and the mixture was then cooled and taken up in 1 liter of water. The solution was made alkaline with concentrated ammonium hydroxide and was extracted with methylene chloride. The organic extracts were dried over sodium sulfate and evaporated to dryness under reduced pressure to obtain 31.4 g of raw product. The said product together with 37 g of the same product produced by an earlier procedure was chromatographed over silica gel and was eluted with a 90-5-5 methylene chloride-methanol-triethylamine mixture to obtain a homogenous fraction of 16 g of product which was taken up in 100 ml of methylene chloride. The mixture was filtered and the filtrate was evaporated to dryness under reduced pressure to obtain 2-nitro-7-methylamino-6,7-dihydro[5H] benzocycloheptene.

The said base was taken up in 160 ml of methanol and 20 ml of a solution of 17 g/100ml of gaseous hydrogen chloride in ethyl acetate were added dropwise at 10° C. thereto. 420 ml of ethyl acetate were added and the mixture was concentrated under reduced pressure and was vacuum filtered. The recovered precipitate was washed with ethyl acetate and ether and dried to obtain 18 g of 2-nitro-7-methylamino-6,7-dihydro [5H] benzocycloheptene hydrochloride in the form of white crystals melting at about 220° C.

EXAMPLE 2

2-amino-7-methylamino-6,7-dihydro [5H] benzocycloheptene furmarate

A mixture of 26 ml of fuming hydrochloric acid, 3.9 g of stannous chloride dihydrate and 1.3 g of 2-nitro-7-methylamino-6,7-dihydro [5H] benzocycloheptene hydrochloride was stirred at room temperature for 16 hours and was then cooled to 10° C. for the addition of 100 ml of water. The mixture was made alkaline at 10° C. with concentrated ammonium hydroxide and was then extracted 3 times with 50 ml of methylene chloride. The organic extracts were washed with water, dried over sodium sulfate and evaporated to dryness under reduced pressure to obtain 1 g of 2-amino-7-methylamino-6,7-dihydro [5H] benzocycloheptene in the form of a brown oil.

The 1 g of the said product was dissolved in 80 ml of methanol and 590 mg of fumaric acid were added thereto. The mixture was concentrated to 20 ml and was allowed to stand and was vacuum filtered to obtain 1.3 g of 2-amino-7-methylamino-6,7-dihydro [5H] benzocycloheptene fumarate in the form of yellow crystals melting at 218° C.

Analysis: $C_{12}H_{16}N_2 \cdot C_4H_4O_4$; molecular weight=304.34. Calculated: %C 63.14; %H 6.62; %N 9.21. Found: %C 62.8; %H 6.9; %N 8.9.

EXAMPLE 3

2-methoxy-7-methylamino-6,7-dihydro [5H] benzocycloheptene hydrochloride 5.1 g of nitrosyl sulfuric acid were added over 10 minutes at 20° C. to a mixture of 6 g of 2-amino-7-methylamino-6,7-dihydro [5H] benzocycloheptene in 60 ml of acetic acid and the mixture was stirred 2 hours at room temperature. The resulting brown solution was poured into 300 ml of methanol and the mixture was refluxed for 45 minutes and was evaporated to dryness under reduced pressure. The residue was added to 150 ml of water and the neutral fraction was removed by extraction twice with 100 ml of ether. The mixture was alkalinized at 10° C. by addition of sodium hydroxide and was extracted with methylene chloride. The organic phase was washed with water, dried over magnesium sulfate, filtered and evaporated to dryness under reduced pressure to obtain 3.7 g of raw product. The latter was chromatographed over silica gel and was eluted with a 7-2-1 chloroform-methanol-triethylamine mixture to obtain a homogenous fraction of 3.4 g of 2-methoxy-7-methylamino-6,7-dihydro [5H] benzocycloheptene in the form of a yellow oil.

The said product was dissolved in 10 ml of ethyl acetate and an ethyl acetate solution saturated with gaseous hydrogen chloride was added thereto dropwise until the pH was 2. The mixture was vacuum filtered to obtain 3.6 g of 2-methoxy-7-methylamino-6,7-dihydro [5H] benzocycloheptene hydrochloride in the form of orange crystals melting at 180° C.

Analysis: $C_{13}H_{17}NO$ . HCl; molecular weight=239.735. Calculated: %C 65.13; %H 7.57; %N 5.84; %Cl 14.79. Found: %C 65.1; %H 7.8; %N 5.8; %Cl 15.0.

EXAMPLE 4

7-methylamino-6,7-dihydro [5H] benzocycloheptene-2-ol hydrochloride

A solution of 2.05 g of sodium nitrite in 20 ml of water was added dropwise over 10 minutes at 5° C. to a mixture of 5.4 g of 2-amino-7-methylamino-6,7-dihydro [5H] benzocycloheptene in 50 ml of 6 N sulfuric acid and the mixture was stirred at 5° C. for 30 minutes to obtain a solution of the salt of the diazonium derivative of 2-amino-7-methylamino-6,7-dihydro [5H] benzocycloheptene. A mixture of 50 ml of water and 10 ml of concentrated sulfuric acid was heated to about 75° C. and the above solution was added thereto dropwise over 10 minutes. The mixture was stirred at 75° C. for 30 minutes and after cooling to 20° C., the neutral fraction was removed by twice extracting with 100 ml of ether. The mixture was cooled to 10° C. and was made alkaline with sodium hydroxide. The non-phenolic fraction was extracted twice with 100 ml of ether and the organic phase was washed twice with 50 ml of sodium hydroxide. The combined aqueous phases were acidified at 10° C. with concentrated hydrochloric acid and the acid phase was then made alkaline at 10° C. with concentrated ammonium hydroxide. The mixture was extracted 3 times with methylene chloride and the organic phase was dried over magnesium sulfate, filtered and evaporated to dryness under reduced pressure to obtain 4 g of product which was crystallized from methylene chloride to obtain 3.5 g of 7-methylamino-6,7-dihydro [5H] benzocycloheptene-2-ol melting at 152° C.

A solution of ethyl acetate saturated with gaseous hydrogen chloride was added dropwise at 10° C. to a solution of 3.5 g of the above product in 35 ml of methanol and 100 ml of ethyl acetate were added thereto. The mixture was concentrated to 50 ml and was vacuum filtered to obtain 3.3 g of 7-methylamino-6,7-dihydro [5H] benzocycloheptene hydrochloride in the form of yellow crystals melting at 215° C.

Analysis: $C_{12}H_{15}NO$ . HCl; molecular weight=225.72. Calculated: %C 63.85; %H 7.15; %N 6.20. Found: %C 63.5; %H 7.1; %N 6.3.

EXAMPLE 5

2-nitro-7-dimethylamino-6,7-dihydro [5H] benzocycloheptene hydrochloride

Using the procedure of Example 1, 3-nitro-8,9-dihydro [5H] benzocycloheptene-5-one and dimethylamine were reacted to obtain a non-salified product which was treated in ethyl acetate with a solution of ethyl acetate saturated with gaseous hydrogen chloride to obtain a product which was crystallized from isopropanol to obtain 2-nitro-7-dimethylamino-6,7-dihydro [5H] benzocycloheptene hydrochloride melting at 202° C.

EXAMPLE 6

Tablets were prepared containing 25 mg of 2-nitro-7-methylamino-6,7-dihydro [5H] benzocycloheptene hydrochloride or 25 mg of 2-methoxy-7-methylamino-6,7-dihydro [5H] benzocycloheptene hydrochloride and sufficient of lactose, starch, talc and magnesium stearate for a final weight of 200 mg.

PHARMACOLOGICAL STUDY

A. Potentialization of effects of monoamine oxidase inhibitor

The administration of a monoamine oxidase inhibitor to mice induces a hyperactive movement of the animals which is able to be potentialized by an antidepressant. Using the procedure of Carlsson et al [Brain Research, Vol. 12 (1969), p. 456], a dose of 100 mg/kg of nialamide was intraperitoneally administered to mice 30 minutes before the intraperitoneal administration of the tested product and the values of actimetric measurements were recorded every 30 minutes for 6 hours. Potentialization of the effects of nialamide for the tested product was expressed in increasing number of + signs for a determined dose in mg/kg. The results are reported in Table I.

TABLE I

| Product of Example | Potentialization of Nialamide in mg/kg |
|---|---|
| 1 | +5 |
|   | ++20 |
| 2 | +5 |
|   | ++20 |
| 3 | +1 |
|   | ++5 |

The results of Table I show that the tested products have an important potentialization of nialamide effects.

B. Potentialization of 5 HTP effects

The administration of 5-hydroxytryptophane (5 HTP) to mice pretreated with an antidepressant induces in the mice a particular behaviour namely the appearance of trembling.

The test product was intraperitoneally administered in increasing doses one hour before the intraperitoneal administration of 200 mg/kg of 5-HTP and the symptoms were observed were noted every 15 minutes for one hour to determine the minimum active dose (MAD) of the test product. The results are reported in Table II.

TABLE II

| Product of Example | MAD in mg/kg |
|---|---|
| 1 | 10 |
| 2 | 5 |

The results show that the products have an important potentialization of the effects of 5 HTP.

C. Potentialization of effects of L-dopa

The administration of L-dopa to mice pretreated 18 hours previously with iproniazide produced certain number of symptoms; muscular hypertonicity, hyperactivity, agitation, crying, aggressiveness, salivation and exophthalmy. The intensity of these effects is potentialized by administration of an antidepressant one hour before the administration of L-dopa. Male mice received intraperitoneally 75 mg/kg of iproniazide 18 hours before the start of the test and the tested product was intraperitoneally administered in aqueous solution in increasing doses. One hour later, L-dopa was intraperitoneally administered at a dose of 100 mg/kg and the different symptoms were observed 15 and 30 minutes later. They were evaluated on a scale of 0 to 3 for each animal and the totals for each dose were determined. The $ED_{50}$ dose which potentializes by 50% the L-dopa effects was determined and is reported in Table III.

TABLE III

| Product of Example | $ED_{50}$ in mg/kg |
|---|---|
| 1 | 1 |
| 2 | 10 |
| 3 | 5 |

The results of Table III show that the tested products potentialize in an important manner the effects of L-dopa.

D. Acute toxicity

The $DL_{50}$ dose which kills 50% of mice after intraperitoneal administration of the tested compound was determined 48 hours later and the $DL_{50}$ for the compounds is reported in Table IV.

TABLE IV

| Product of Example | $DL_{50}$ in mg/kg |
|---|---|
| 1 | 75 |
| 2 | 75 |
| 3 | 50 |
| 4 | 50 |

BIOCHEMICAL STUDY

A. Inhibition of Serotonine uptake in vitro

The inhibition of serotonine (5HT) uptake was measured in impure synaptosomes prepared from the entire brain of a female rat 19 to 21 days old using the technique of Kannengiesser et al. [Biochemical Pharmacology, Vol. 22, (1973) p. 73]. Diverse concentrations of the products were placed in an incubator with the preparation at 37° C. for 5 minutes in the presence of 14 C-5HT at a concentration of $10^{-7}$ M. The 50% inhibiting concentration ($IC_{50}$), dose which inhibits by 50% the uptake of 14C-5HT in the synaptosomes was determined graphically and the $IC_{50}$ dose for the compounds is reported in Table V.

B. Inhibition of Serotonine uptake in vivo

The tested products were intraperitoneally administered to groups of female rats 19 to 21 days old at doses of 5 to 20 mg/kg. After 30 minutes, the brain was removed and synaptosomes were prepared and placed in an incubator in the presence of 14 C-5HT as indicated in the previous test. The relative power of the products to inhibit the uptake of 14C-5HT was estimated with respect to a test effected with animals which did not receive the tested product and the activity was expressed in increasing number of + signs. The results are reported in Table V.

TABLE V

| Product of Example | Test in vitro I.C. 50 (M) | In vivo Test |
|---|---|---|
| 1 | $3.2 \times 10^{-7}$ | +++ |
| 2 | $4.0 \times 10^{-6}$ | + |
| 3 | $2.7 \times 10^{-7}$ | ++ |
| 4 | $3.8 \times 10^{-7}$ | |

The results of Table V show that the tested products have an interesting activity against serotonine.

Various modifications of the products and methods of the invention may be made without departing from the spirit or scope thereof and it should be understood that the invention is intended to be limited only as defined in the appended claims.

We claim:

1. A compound selected from the group consisting of 7-aminobenzocycloheptenes of the formula

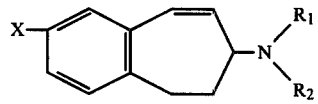

wherein X is selected from the group consisting of $-NO_2$, $-NH_2$, $CH_3O-$ and $-OH$, $R_1$ is selected from the group consisting of hydrogen and alkyl of 1 to 5 carbon atoms, $R_2$ is alkyl of 1 to 5 carbon atoms and their non-toxic, pharmaceutically acceptable acid addition salts in optically active or racemic mixture form.

2. A compound of claim 1 wherein $R_1$ is hydrogen or methyl and $R_2$ is methyl.

3. A compound of claim 2 wherein $R_1$ is hydrogen.

4. A compound of claim 1 selected from the group consisting of 2-nitro-7-methylamino-6,7-dihydro [5H] benzocycloheptene and its non-toxic, pharmaceutically acceptable acid addition salts.

5. A compound of claim 1 selected from the group consisting of 2-amino-7-methylamino-6,7-dihydro [5H] benzocycloheptene and its non-toxic, pharmaceutically acceptable acid addition salts.

6. A compound of claim 1 selected from the group consisting of 2-methoxy-7-methylamino-6,7-dihydro [5H] benzocycloheptene and its non-toxic, pharmaceutically acceptable acid addition salts.

7. A compound of claim 1 selected from the group consisting of 7-methylamino-6,7-dihydro [5H] benzocycloheptene-2-ol and its non-toxic, pharmaceutically acceptable acid addition salts.

8. A compound of claim 1 selected from the group consisting of 2-nitro-7-dimethylamino-6,7-dihydro [5H] benzocycloheptene and its non-toxic, pharmaceutically acceptable acid addition salts.

9. An antidepressive composition comprising an antidepressively effective amount of at least one compound of claim 1 and an inert pharmaceutical carrier.

10. A composition of claim 9 wherein $R_1$ is selected from the group consisting of hydrogen and alkyl of 1 to 5 carbon atoms and $R_2$ is alkyl of 1 to 5 carbon atoms.

11. A composition of claim 9 wherein $R_1$ is hydrogen or methyl and $R_2$ is methyl.

12. A composition of claim 11 wherein $R_1$ is hydrogen.

13. A method of relieving depression in warm-blooded animals comprising administering to warm-blooded animals an antidepressantly effective amount of at least one compound of claim 1.

14. A method of claim 13 wherein $R_1$ is hydrogen or methyl and $R_2$ is methyl.

15. A method of claim 14 wherein $R_1$ is hydrogen.

* * * * *